United States Patent
Lind et al.

(10) Patent No.: US 6,468,518 B2
(45) Date of Patent: Oct. 22, 2002

(54) DELIQUESCENT SALT ADDITION TO ALUM USED TO TREAT ANIMAL WASTE PRODUCTS

(75) Inventors: Christopher Bruce Lind, Syracuse; Joseph Lewis Hurd, Sandy Creek, both of NY (US); Russell Hayden Barnes, Salisbury, MD (US)

(73) Assignee: General Chemical Corporation, Parsippany, NJ (US)

( * ) Notice: Subject to any disclaimer, the term of this patent is extended or adjusted under 35 U.S.C. 154(b) by 0 days.

(21) Appl. No.: 09/779,061

(22) Filed: Feb. 8, 2001

(65) Prior Publication Data

US 2002/0106344 A1 Aug. 8, 2002

(51) Int. Cl.$^7$ .................... A61L 11/00; A61K 39/395; A01K 29/00
(52) U.S. Cl. .................... 424/76.6; 424/76.1; 424/76.5; 424/131; 424/141; 424/144; 424/147; 424/600; 424/682; 424/698; 119/171
(58) Field of Search .................... 424/76.1, 76.5, 424/76.6, 141, 131, 144, 147, 600, 682, 698; 119/171

(56) References Cited

U.S. PATENT DOCUMENTS

| | | | |
|---|---|---|---|
| 4,770,878 A | | 9/1988 | Thomas ................ 424/141 |
| 5,622,697 A | | 4/1997 | Moore, Jr. ................ 424/693 |
| 5,865,143 A | | 2/1999 | Moore, Jr. ................ 119/442 |
| 5,890,454 A | * | 4/1999 | Moore, Jr. ................ 119/447 |
| 5,914,104 A | | 6/1999 | Moore, Jr. ................ 424/76.6 |
| 5,928,403 A | | 7/1999 | Moore, Jr. ................ 71/21 |
| 5,945,333 A | * | 8/1999 | Rehberger ................ 435/268 |
| 5,960,743 A | * | 10/1999 | Taylor ................ 119/173 |
| 5,961,968 A | | 10/1999 | Moore, Jr. ................ 424/76.6 |

* cited by examiner

Primary Examiner—Thurman K. Page
Assistant Examiner—Charesse L. Evans
(74) Attorney, Agent, or Firm—Arthur J. Plantamura

(57) ABSTRACT

Animal enclosures such as poultry houses generate high amounts of ammonia that adversely affect weight gain and mortality or the animals, particularly among young chicks. The addition of a deliquescent salt, such as calcium chloride, to alum to treat animal waste products rapidly activates the alum to remove ammonia from the atmosphere. The ammonia sulfate by-product is useful as a nitrogen fertilizer.

26 Claims, 1 Drawing Sheet

DELIQUESCENT SALT ADDITION TO ALUM USED TO TREAT ANIMAL WASTE PRODUCTS

This invention relates to improvements in the treatment of animal litter with alum to reduce the generation of ammonia in the litter. More particularly, this invention relates to the addition of a deliquescent salt to alum to increase the absorption of water by the alum to speed the reaction of alum with ammonia.

BACKGROUND OF THE INVENTION

Moore, Jr., in a series of U.S. patents, has explained that animal litter or manure, particularly from farm animals such as poultry and pigs, contains ammonia and phosphates. The amounts of ammonia given off into the atmosphere adversely affects farm workers, and even the animals themselves. When large amounts of ammonia are present in the atmosphere of animal enclosures, the result is lower weight gain and higher mortality rates for the animals.

Thus alum (aluminum sulfate), having the formula $Al_2(SO_4)_3 \cdot nH_2O$ wherein n above 1 and typically is about 14–18, has been used to reduce the pH, and thus the ammonia generation, of manure and animal bedding material. Alum, either in solid or liquid form, will lower the pH of the manure by hydrolysis and will convert ammonia to ammonium ions. Ammonium ions will react with sulfates to form ammonium sulfate; the latter is a water soluble nitrogen fertilizer and can be used as such. Desirably, the amount of ammonia present in the atmosphere of an animal enclosure should be held below about 25 ppm. The use of alum for this purpose has an added advantage in that the soluble phosphates present precipitate in the presence of aluminum and thus the soluble phosphate content of manure is also reduced by this treatment. Soluble phosphates are known to seep into ground water or are carried in surface runoff water. In either case, this presents a substantial environmental problem.

Dry alum can require up to two weeks to absorb sufficient water from the air or surrounding litter to initiate the reduction of the pH of litter and thereby reduce ammonia production. Alum can be mixed with water and sprayed onto manure in an effort to accelerate its function, but this may require additional handling and it reduces the flexibility of the application timing with respect to the placement of chicks, for example, in an enclosure. The addition of water also introduces a detrimental effect on the humidity of the house and the litter.

Other sulfates can be used in place of alum or in conjunction therewith, but they must have or must cause, a low pH. Thus iron sulfate can be used, but is undesirable from a bird health standpoint if the iron sulfate is ingested in excess.

SUMMARY OF THE INVENTION

In accordance with the present invention, we have discovered that a deliquescent salt, when added to dry alum, can improve the absorption of water by the alum, thereby solubilizing the alum, and allowing the alum to react with ammonia. The time required for the solubilization of alum is called the activation time, and it indicates absorption of water by the alum. This activation time can be reduced from about two weeks in a dry atmosphere to as little as twenty-four hours when a deliquescent salt is added to the alum. The presence of the deliquescent salt also improves the uniformity of the moisture in the litter composition.

DETAILED DESCRIPTION OF THE INVENTION

Figure 1:
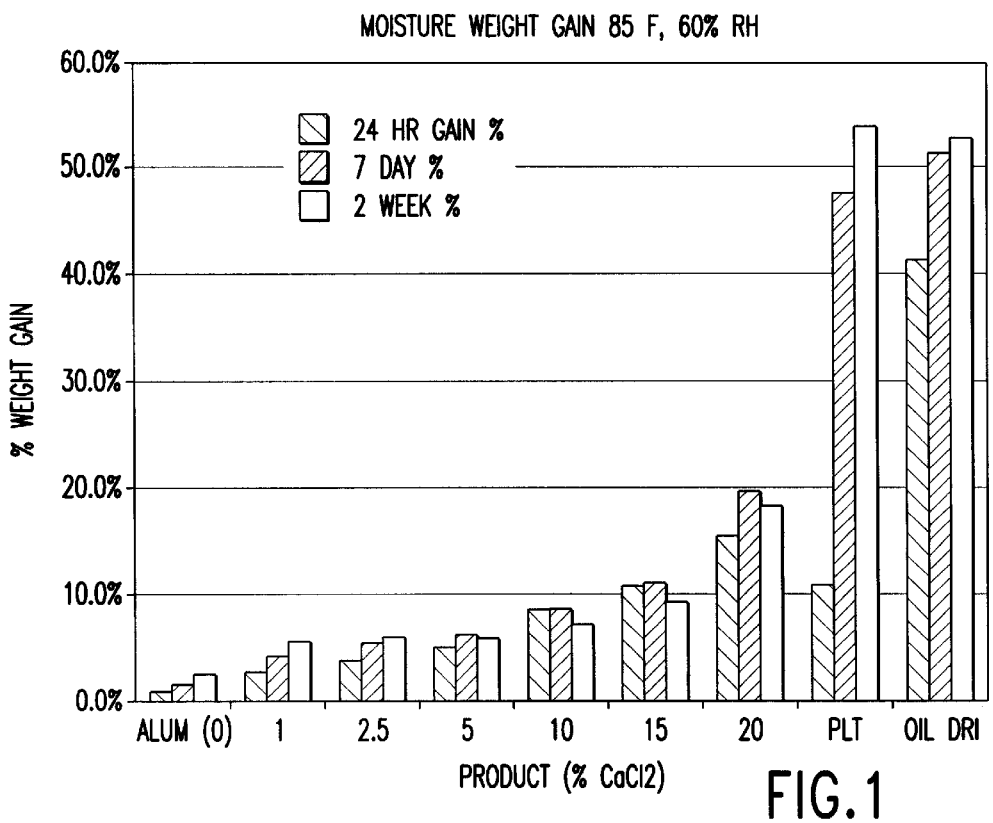
FIG. 1 is a graph of weight gain due to moisture absorption over time for alum alone, and for alum mixed with calcium chloride.

In accordance with the invention, a deliquescent salt activator is added to dry alum in amounts of from 1 to 30 percent by weight, preferably about 10–20 percent by weight. The activator can be pre-mixed with alum, but preferably is either added just prior to applying alum to animal litter, bedding or manures, or immediately after alum application, as with drop or rotary spreaders. The two materials are thus in intimate contact. That is, the activator is applied to manure or litter or other bedding mixture, followed by alum addition on top of and along with the activator. Alum can also be applied as before with the activator spread on top of, or along with, the alum. The introduction of moisture to dry alum, preferably effected by the presence of a deliquescent activator, initiates hydrolysis and reduces the pH of the manure and litter, which in turn inhibits the release of ammonia into the atmosphere.

Suitable litter compositions can include a mixture of one or more of wood shavings, secondary paper, nut hulls, bran hulls, rice hulls, wood chips, sand and sawdust as examples. Other materials are known to those skilled in the art.

Suitable deliquescent materials include chlorides such as magnesium chloride, calcium chloride, manganese chloride, ferric chloride and zinc chloride; and other metal salts including ammonium citrate, calcium chlorate, calcium iodide, calcium nitrite, calcium nitrate, cobaltous ammonium chloride, cobaltous iodide, cupric chlorate, cupric nitrate, ferric chloride, ferric lactate, ferric nitrate, ferrous iodide, magnesium ammonium chloride, magnesium nitrate, magnesium nitrite, manganese oxide, manganese sulfate, phosphoric acid, phosphorus oxide, potassium acetate, potassium carbonate, potassium iodide, potassium phosphate, sodium bisulfate, sodium acetate, stannic sulfate and zinc chloride.

Deliquescent salts including calcium chloride, magnesium chloride, sodium bisulfate, manganese chloride, zinc chloride, anhydrous ferric chloride, magnesium nitrate, calcium nitrate, potassium acetate and sodium acetate, are preferred. Since some of the above deliquescent salts may have adverse effects on some animals, such as poultry chicks, the amounts of the salts must be regulated to avoid harmful doses. The addition of the deliquescent material is also regarded as aiding control of nuisance dust in the animal housing.

Calcium chloride, being a very effective deliquescent material, absorbs moisture from the atmosphere, even very dry atmospheres, until a solution is formed; this absorbed water becomes the activator for alum.

In comparative tests, unmodified alum in a dry atmosphere gained only 1% by weight of water in a given period of time. Other materials, such as "PLT" a product of Jones Hamilton Co., made of sodium bisulfate and sodium sulfate, and "Poultry Guard", a brand name of Oil Dri Co., comprising mixtures of a clay material (Fuller's Earth) and sulfuric acid, gained 11–41% by weight of water in a comparable time. However, these materials provide only a relatively temporary effectiveness, on the order of 3–5 days. The effectiveness of the present alum treatments affords a relatively long lasting effectiveness of greater than two weeks.

The addition of about 10–30% by weight of calcium chloride to dry alum results in activated alum within about 24 hours. Thus the distribution of the mixed deliquescent salt-alum to a poultry enclosure, preferably 1–4 days prior to chicks being placed in the enclosure, but as many as seven days prior, shortens the activation time and ensures that an activated alum product is present in time to reduce ammonia formation.

Calcium chloride, either as a dry material in dry flake, pellet or dry powder form, or as a liquid solution in about 32% by weight strength, is mixed with dry alum in amounts of about 1–30% by weight at such time as is suitable to form an activated alum. Preferably, the deliquescent salt is added to alum just prior to application to a prepared surface, i.e., to livestock or poultry bedding, and prior to animals being placed on the prepared bedding.

Although calcium chloride is referred to above, other deliquescent materials can be partially or wholly substituted as noted hereinabove.

Unmodified alum can gain as little as 1% by weight of water in a dry atmosphere, whereas the addition of an activator, such as calcium chloride, to the alum results in water absorption of from about 3% up to about 15% by weight in 24–72 hours. Once animals are placed on the bedding mixture, alum readily absorbs free water from drinkers and animal waste.

FIG. 1 illustrates the weight gain due to moisture absorption by alum alone, by alum mixed with varying amounts of from 1% up to 30% by weight of calcium chloride, and moisture absorption by two commercially available products, maintained at an atmosphere of 60% RH and a temperature of about 85° F. Weight gain was measured after 24 hours, after one week, and after two weeks. Amounts of calcium chloride of from about 5–15% by weight results in good, and about equal, water absorption over a period of one to two weeks. It can be seen that even when a minimum amount of calcium chloride is added, the moisture gain is both rapid and stable over a two week period. It is apparent that the addition of calcium chloride improves water absorption by alum, particularly in the initial 24 hour period.

The pH was measured after one week for 1% and 5% by weight calcium chloride addition. The addition of calcium chloride slightly lowered the pH.

Litter moisture should be kept low, generally less than or equal to about 20% by weight.

It is apparent that other products containing sulfates, while they have a higher initial moisture content, continue to gain in moisture content rapidly during a one week period, and continue to rise more slowly after that. Thus the moisture content of the alum product is much more stable when using calcium chloride.

The absorption of too much water by litter or manure can have a detrimental effect because wet, even damp, manure tends to reduce weight gain performance and serves to provide a hospitable environment for the generation of pathogens in manure. Wet litter may enhance the presence of pathogen vectors and destructive insects, i.e., flies and beetles, which disturb animals and reduce feed conversion to weight gain. The removal of wet, and therefore heavy, manure and bedding is also more difficult and more expensive.

Further, the presence of calcium or magnesium does not significantly reduce the phosphorus binding capacity of alum, since calcium and magnesium compounds, including calcium chloride, precipitate the phosphorus.

Figure 2:
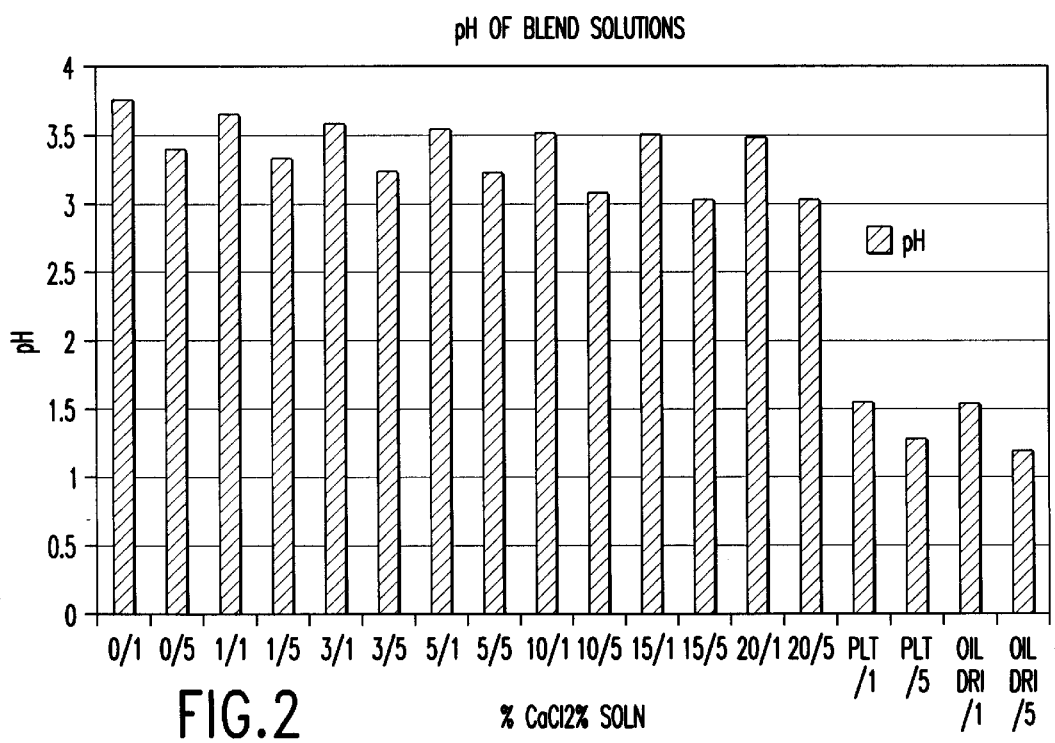
FIG. 2 is a graph showing the variation in pH with increased calcium chloride addition to alum.

FIG. 2 shows the variation in pH with increasing calcium chloride addition as a 2% by weight solution with alum. The pH is maintained at from at least 3 and up to about 3.5 at all levels of calcium chloride addition.

Commercially available products such as those of PLT and Oil Dri described hereinabove, while having a lower pH due to the presence of high amounts of sulfuric acid, are found to have lower or no buffering effects.

The addition of increased amounts of calcium chloride in the blend will further reduce the pH.

Preferably calcium chloride or other deliquescent salt is added to dry alum in a typical treatment just prior (about 1–4 days) to placing animals in their enclosure.

The calcium chloride-alum mixture is applied at about 50–200 lbs/1000 ft$^2$ of treated area. The mixture can be applied to the entire enclosure, or to less than the entire enclosure, and is particularly useful in brood chambers.

The present treatment methods are highly effective in housing for animals including poultry, including chickens, turkeys and ducks, and sine, cattle, lambs, rabbits and rodents.

Although the invention has been described in terms of specific additives and amounts, other additives can be added as will be known to one skilled in the art. Thus the invention is only meant to be limited by the scope of the appended claims.

We claim:

1. A method of reducing ammonia generation in animal enclosures comprising
    adding a dry mixture of aluminum sulfate and a deliquescent salt in amounts of between about one percent and 30 percent based on the weight of aluminum sulfate.
2. A method according to claim 1 wherein the deliquescent salt is selected from the group consisting of calcium chloride, manganese chloride, ferric chloride, zinc chloride, ammonium citrate, calcium chlorate, calcium iodide, calcium nitrite, calcium nitrate, cobaltous ammonium chloride, cobaltous iodide, cupric chlorate, cupric nitrate, ferric lactate, ferric nitrate, ferrous iodide, magnesium ammonium chloride, magnesium chloride, manganese oxide, manganese sulfate, phosphoric acid, phosphorus oxide, potassium acetate, potassium carbonate, potassium iodide, potassium phosphate, sodium bisulfate, sodium acetate, stannic sulfate and zinc chloride.
3. A method according to claim 1 wherein the deliquescent salt is selected from the group consisting of calcium chloride, magnesium chloride, sodium bisulfate, manganese chloride, zinc chloride, anhydrous ferric chloride, magnesium nitrate, calcium nitrate, potassium acetate and sodium acetate.
4. A method according to claim 1 wherein the deliquescent salt is calcium chloride.
5. A method according to claim 1 wherein the deliquescent salt is magnesium chloride.
6. A method according to claim 1 wherein the deliquescent salt is sodium bisulfate.
7. A method according to claim 1 wherein the deliquescent salt is added in sequence following the addition of alum.
8. A method according to claim 1 wherein the addition of alum follows in sequence the addition of the deliquescent salt.
9. A method according to claim 4 wherein calcium chloride is added in an amount of from about 10 to 30 percent by weight of the aluminum sulfate.
10. A method according to claim 9 wherein magnesium chloride is added in an amount of from 10 to 30 percent by weight of aluminum sulfate.

11. A method according to claim 1 wherein the deliquescent salt is added as a calcium chloride aqueous solution at a strength of about 35 percent by weight.

12. A method according to claim 1 wherein the deliquescent salt is added as a magnesium chloride aqueous solution at a strength of about 32 percent by weight.

13. A method of reducing the ammonia content of the atmosphere in an animal enclosure to below about 25 parts per million comprising adding a dry mixture of aluminum sulfate and from 1 to 30 percent by weight of a deliquescent salt to animal wastes.

14. A method according to claim 13 wherein said deliquescent salt is selected from the group consisting of calcium chloride, magnesium chloride, sodium bisulfate, manganese chloride, zinc chloride, anhydrous ferric chloride, magnesium nitrate, calcium nitrate, potassium acetate and sodium acetate.

15. A method according to claim 13 wherein said deliquescent salt is calcium chloride.

16. A method according to claim 13 wherein said deliquescent salt is magnesium chloride.

17. A method according to claim 13 wherein said deliquescent salt is sodium bisulfate.

18. A method according to claim 1 wherein said animals are selected from the group consisting of poultry, swine, cattle, lamb, rabbits and rodents.

19. A method according to claim 18 wherein said poultry includes chickens, turkeys and ducks.

20. A litter composition comprising a dry mixture of one or more of wood shavings, secondary paper, nut hulls, bran hulls, rice hulls, wood chips, sand and sawdust, and including alum in combination with an activator.

21. A litter composition according to claim 20 wherein the activator is a deliquescent salt.

22. A litter composition according to claim 20 wherein the activator is calcium chloride.

23. A litter composition according to claim 20 wherein the activator is sodium bisulfate.

24. A litter composition according to claim 20 wherein the activator is magnesium chloride.

25. A dry blend of alum and a deliquescent salt activator in amounts of from about one percent to about 30 percent by weight of the activator for treating animal litter and suppressing the generation of ammonia.

26. A blend in accordance with claim 25 wherein the activator is calcium chloride present in amounts of about 15 percent to about 30 percent based on the weight of aluminum sulfate.

* * * * *

UNITED STATES PATENT AND TRADEMARK OFFICE
Certificate

Patent No. 6,468,518 B2                                            Patented: October 22, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christopher Bruce Lind, Syracuse, NY; Joseph Lewis Hurd, Sandy Creek, NY; Russell Hayden Barnes, Salisbury, MD; and Philip A. Moore, Jr., Fayetteville, AK.

Signed and Sealed this Twenty-first Day of September 2004.

<div style="text-align:right">

THURMAN K. PAGE
*Supervisory Patent Examiner*
Art Unit 1615

</div>